US008328714B2

(12) United States Patent
Couvillon, Jr.

(10) Patent No.: US 8,328,714 B2
(45) Date of Patent: *Dec. 11, 2012

(54) ROBOTIC ENDOSCOPE

(75) Inventor: Lucien Alfred Couvillon, Jr., Concord, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 83 days.

This patent is subject to a terminal disclaimer.

(21) Appl. No.: 12/697,893

(22) Filed: Feb. 1, 2010

(65) Prior Publication Data
US 2010/0137688 A1 Jun. 3, 2010

Related U.S. Application Data

(63) Continuation of application No. 10/951,263, filed on Sep. 27, 2004, now Pat. No. 7,666,135, which is a continuation of application No. 09/971,419, filed on Oct. 5, 2001, now Pat. No. 6,835,173.

(51) Int. Cl.
*A61B 1/00* (2006.01)

(52) U.S. Cl. ........ 600/146; 600/114; 600/117; 600/151; 600/152; 604/95.01

(58) Field of Classification Search ................ 600/114, 600/117, 146, 151, 152; 604/95.01
See application file for complete search history.

(56) References Cited

U.S. PATENT DOCUMENTS

| | | | |
|---|---|---|---|
| 4,273,111 A | 6/1981 | Tsukaya | |
| 4,286,585 A | 9/1981 | Ogawa | |
| 4,499,895 A | 2/1985 | Takayama | |
| 4,503,842 A | 3/1985 | Takayama | |
| 4,543,090 A | 9/1985 | McCoy | |
| 4,601,705 A | 7/1986 | McCoy | |
| 4,753,223 A | 6/1988 | Bremer | |
| 4,790,624 A | 12/1988 | Van Hoye et al. | |
| 4,832,473 A | 5/1989 | Ueda | |
| 4,846,573 A | 7/1989 | Tayler et al. | |
| 4,884,557 A | 12/1989 | Takehana et al. | |
| 4,899,731 A | 2/1990 | Takayama et al. | |
| 4,930,494 A | 6/1990 | Takehana et al. | |
| 4,977,886 A | 12/1990 | Takehana et al. | |
| 4,987,314 A | 1/1991 | Gotanda et al. | |
| 5,090,956 A | 2/1992 | McCoy | |

(Continued)

FOREIGN PATENT DOCUMENTS

ES 2 048 086 1/1992

(Continued)

OTHER PUBLICATIONS

"Active Endoscope (ELASTOR, Shape Memory Alloy Robot)," http://mozu.mes.titech.ac.jp/research/medical/endoscope/endoscope.html, 9 pages including 3 Figures and 4 photographs, downloaded prior to Oct. 5, 2001.

(Continued)

*Primary Examiner* — Aaron Roane
(74) *Attorney, Agent, or Firm* — Mayer & Williams PC; David B. Bonham; Keum J. Park

(57) ABSTRACT

An endoscope is provided which comprises an elongated body adapted for insertion into a body lumen, and a plurality of electrically controlled actuators associated with the body which are controllable to impart an orientation to the body that is complimentary to the natural orientation of the lumen into which the endoscope is inserted.

18 Claims, 9 Drawing Sheets

U.S. PATENT DOCUMENTS

| | | | |
|---|---|---|---|
| 5,188,111 A | 2/1993 | Yates et al. | |
| 5,239,982 A | 8/1993 | Trauthen | |
| 5,250,167 A | 10/1993 | Adolf et al. | |
| 5,268,082 A | 12/1993 | Oguro et al. | |
| 5,337,732 A | 8/1994 | Grundfest et al. | |
| 5,347,987 A | 9/1994 | Feldstein et al. | |
| 5,389,222 A | 2/1995 | Sahahinpoor | |
| 5,396,879 A | 3/1995 | Wilk et al. | |
| 5,431,645 A | 7/1995 | Smith et al. | |
| 5,482,029 A | 1/1996 | Sekiguchi et al. | |
| 5,492,131 A | 2/1996 | Galel | |
| 5,556,370 A | 9/1996 | Maynard | |
| 5,556,700 A | 9/1996 | Kaneto et al. | |
| 5,624,380 A | 4/1997 | Takayama et al. | |
| 5,631,040 A | 5/1997 | Takuchi et al. | |
| 5,645,520 A | 7/1997 | Nakamura et al. | |
| 5,651,366 A | 7/1997 | Liang et al. | |
| 5,662,587 A | 9/1997 | Grundfest et al. | |
| 5,771,902 A | 6/1998 | Lee et al. | |
| 5,819,749 A | 10/1998 | Lee et al. | |
| 5,855,565 A | 1/1999 | Bar-Cohen et al. | |
| 5,873,817 A | 2/1999 | Kokish et al. | |
| 5,906,591 A | 5/1999 | Dario et al. | |
| 5,916,146 A | 6/1999 | Allota et al. | |
| 5,957,833 A | 9/1999 | Shan | |
| 6,071,234 A | 6/2000 | Takada | |
| 6,109,852 A | 8/2000 | Shahinpoor et al. | |
| 6,162,171 A | 12/2000 | Ng et al. | |
| 6,249,076 B1 | 6/2001 | Madden et al. | |
| 6,293,907 B1 | 9/2001 | Axon et al. | |
| 6,468,203 B2 | 10/2002 | Belson | |
| 6,514,237 B1 | 2/2003 | Maseda | |
| 6,835,173 B2 * | 12/2004 | Couvillon, Jr. | 600/146 |
| 7,666,135 B2 * | 2/2010 | Couvillon, Jr. | 600/146 |
| 2002/0062062 A1 | 5/2002 | Belson et al. | |

FOREIGN PATENT DOCUMENTS

| | | |
|---|---|---|
| ES | 2 062 930 | 12/1992 |
| JP | 03-004830 | 1/1991 |
| JP | 03-109021 | 5/1991 |
| JP | 03-139325 | 6/1991 |
| JP | 03-170125 | 7/1991 |
| JP | 05-076599 | 3/1993 |
| JP | 05-177002 | 7/1993 |
| JP | 05-184531 | 7/1993 |
| JP | 06-133922 | 5/1994 |
| JP | 07-088788 | 4/1995 |
| JP | 07-120684 | 5/1995 |
| JP | 07-302268 | 11/1995 |
| JP | 08-010336 | 1/1996 |
| JP | 08-066351 | 3/1996 |
| JP | 08-322783 | 12/1996 |
| JP | 08-322786 | 12/1996 |
| JP | 10-014863 | 1/1998 |
| JP | 11-048171 | 2/1999 |
| JP | 11-244225 | 9/1999 |
| JP | 2000-342527 | 12/2000 |
| JP | 2001096478 | 4/2001 |
| JP | 2001-286441 | 10/2001 |
| JP | 2002-085333 | 3/2002 |
| JP | 2002-99627 | 4/2002 |
| JP | 2002-132957 | 5/2002 |
| WO | WO 98/11816 | 2/1998 |
| WO | WO 01/58973 A2 | 8/2001 |

OTHER PUBLICATIONS

"Robot Snake with Flexible Real-Time Control," from http://ais.gmd.de/BAR/snake.html, last updated Jan. 10, 2007.

"Smart Catheters," from http://www.piaggio.ccii.unipi.it/cathe.htm, printed Aug. 27, 2001.

"Snake-like Flexible Micro-robot," from http://www.agip.sciences.univ-metz.fr/mihalach/Copernicus_project_engl.html, Project start: May 1, 1995.

"Snake-like Robot Endoscopes" from http://robby.Caltech.edu/chen/res-medical.html, page updated Aug. 14, 1996.

"Walking machines: 0-legged robots," complied by C. Duntgen, Aug. 26, 2000.

"Worldwide ElectroActive Polymers (Artificial Muscles) Newsletter," vol. 3, No. 1 (Jun. 2001).

Bar Cohen, Smart Structures and Materials 2001: Electroactive Polymer Actuators and Devices, Yoseph Bar-Cohen, Ed., Proceedings of SPIE vol. 4329 (Mar. 5-8, 2001), pp. 1-6.

Bar-Cohen, Ed., Electroactive Polymer (EAP) Actuators as Artificial Muscles, SPIE Press (2001), Chapter 1, pp. 3-44.

Bar-Cohen, Ed., Electroactive Polymer (EAP) Actuators as Artificial Muscles, SPIE Press (2001), Chapter 7, pp. 193-221.

Brock, David L., "Review of Artificial Muscle based on Contractile Polymers," MIT Artificial Intelligence Laboratory, A.I. memo No. 1330, Nov. 1991, pp. 1-12.

Cho, et al., Electroactive Polymer Actuators and Devices, Yoseph Bar-Cohen, Ed., Proceedings of SPIE vol. 4329 (Mar. 5-8, 2001), pp. 466-474.

Della Santa et al., "Intravascular Microcatheters Steered by Conducting Polymer Actuators," Proceedings of the 18th Annual International Conference of the IEEE Engineering in Medicine and Biology Society, vol. 5, 1997, pp. 2203-2204.

Electroactive Polymer (EAP) Actuators as Artificial Muscles, Yoseph Bar-Cohen, Ed., Spie Press (2001), Chapter 16, pp. 457-495.

Electroactive Polymer (EAP) Actuators as Artificial Muscles, Yoseph Bar-Cohen, Ed., SPIE Press (2001), Chapter 21, pp. 615-659.

Ikuta et al., "Shape Memory Alloy Servo Actuator System with Electroic Resistance Feedback and Application for Active Endoscope," IEEE Int'l Conference on Robotics and Automation (Apr. 24-29, 1988), pp. 427-430.

Jager et al., "Microfabricating Conjugated Polymer Actuators," Science, vol. 290 (Nov. 24, 2000), pp. 1540-1545.

Joen, et al., Smart Structures and Materials 2001: Electroactive polymer actuators and Devices, Yoseph Bar-Cohen, Ed., Proceedings of SPIE vol. 4329 (Mar. 5-8, 2001), pp. 380-388.

Kubler et al., "An Endoscopic Navigation System," Processing of Medicine Meets Virtual Reality—MMVR 2001, pp. 253-255.

Kubler et al., "Endoscopic Robots," Proceedings in 3rd International Conference on Medical Image Computing and Computer-Assisted Intervention—MICCAI 2000, pp. 949-955.

Lightdale, MD, "New Developments in Endoscopy", American College of Gastroenterology 65th Annual Scientific Meeting, Oct. 16, 2000, pp. 1-9.

Madden et al., "Polypyrrole actuators: modeling and performance", Mar. 5-8, 2001, Proceedings of SPIE, vol. 4329, pp. 72-83.

Madden et al., Smart Structures and Materials 2001: Electroactive Polymer Actuators and Devices, Yoseph Bar-Choen, Ed., Proceedings of SPIE vol. 4329 (Mar. 5-8, 2001) pp. 72-83.

Madden, John David Wyndham, "conducting Polymer Actuators," Massachusetts Institute of Technology, Sep. 2000.

Mazzoldi et al. "Conductive Polymer Based Structures for a Steerable Catheter," Smart Structures and Materials 2000: Electroactive Polymer Actuators and Devices, Yoseph Bar-Cohen, ed. Proceedings of SPIE, vol. 3987 (2000), pp. 273-280.

Nam, "Electroactive Polymer (EAP) Actuators and Devices for Micro-Robot Systems" Nov. 28, 2000.

Peirs et al., "Miniature Parallel Manipulators for Integration in a Self-propelling Endoscope," IUAP P4/24 IMechS Workshop, Oct. 27, 1999.

Pelrine et al., Smart Structures and Materials 2001: Electroactive Polymer Actuators and Devices, Yoseph Bar-Cohen, Ed., Proceedings of SPIE vol. 4329 (Mar. 5-8, 2001), pp. 335-349.

Slatkin et al., "The Development of a Robotic Endoscope," Proceedings of the 1995 IEEE/RSJ International Conference on Intelligent Robots and Systems: Human Robot Interaction and Cooperative Robots, vol. 2, Aug. 5, 1995, pp. 162-171.

Zuccaro, "Procedural Sedation in the GI Suite" 16th Annual Meeting 2001: May 3-6, 2001.

* cited by examiner

ROBOTIC ENDOSCOPE

STATEMENT OF RELATED APPLICATIONS

This application is a continuation of co-pending U.S. patent application Ser. No. 10/951,263, filed Sep. 27, 2004, now U.S. Pat. No. 7,666,135, which is a continuation of U.S. patent application Ser. No. 09/971,419, filed Oct. 5, 2001, now U.S. Pat. No. 6,835,173, each of which is incorporated by reference in its entirety herein.

FIELD OF THE INVENTION

The present invention relates to robotic endoscopes, and more particularly to robotic endoscopes in which the 3-dimensional shape of the endoscope is controlled.

BACKGROUND OF THE INVENTION

Diagnostic endoscopy is a common procedure in the United States and other countries, perhaps being second only to interventional cardiology in generating hospital revenue.

Traditional endoscopy utilizes flexible endoscopes that are steered by internal tension wires. These probes typically include means for illumination, lavage, and imaging (usually with a CCD camera chip at the distal tip), as well as a working channel through which, for example, biopsy forceps, snares, and fulguration probes can be introduced. Such devices allow physicians to see and treat polyps and other common disorders of the alimentary, gastrointestinal, and respiratory tracts.

Even after 20 years of refinement, present day endoscopes are expensive, bulky and stiff. For example, conventional steering-cable-based schemes allow for control of the shape of only the most distal portion of the endoscope. As a result, a long, relatively stiff portion of the endoscope follows the working tip. The resultant forces imparted to sensitive endolumenal tissue result in the need for sedation. Conventional endoscopes are also subject to cross-contamination, unless they are cleaned and disinfected carefully.

Annual colonoscopic examinations are routinely recommended for males over 50 years of age, but only a small fraction of this population receives such an annual examination, because of the discomfort and the perceived risks associated with the examination. Moreover, present day endoscopic examinations almost always require sedation, for example, using a powerful amnesiac such as midazolam hydrochloride (e.g. Versed® owned by Hoffmann LaRoche). This sedation accounts for approximately half of the costs associated with the overall endoscopic procedure.

There have been several research projects aimed at "sedationless" endoscopy using designs that clamp-and-pull the endoscope using distal inchworm or suck-and-step mechanisms. These approaches do not, however, overcome the disadvantage that the balance of the endoscope is dragged along after the distal end.

There is thus a need for a new generation of endoscopes that can navigate the anatomic tract with minimal tugging and pulling on the endothelium, thus reducing the pain, risk and need for sedation that is associated with endoscopic examinations. This will in turn lead to a decrease in the cost and an increase in the frequency of endoscopic diagnosis and treatment for a wide variety of cancers and other disorders of the aerodigestive system. These and other needs are met by the present invention, as hereinafter described.

SUMMARY OF THE INVENTION

The present invention relates to an endoscope that comprises an elongated body adapted for insertion into an intestinal lumen. A plurality of electrically controlled actuators are associated with the body, and are controllable to impart a desired orientation to the body that reflects, and preferably is complimentary to, the natural orientation or three-dimensional spatial trajectory of the lumen into which the endoscope is inserted. The endoscope may be provided with a sensing system, such as an optical system comprising a light source and a camera, at a distal end of the elongated body for sensing the natural orientation of the lumen into which the endoscope is inserted. The endoscope may also be provided with a driving mechanism for advancing the body through the lumen in accordance with a drive algorithm. Since the endoscopes of the present invention rely on electrically controlled actuators to impart a desired orientation to the body of the device, they do not require traditional steering cables, bulky motors or mechanical joints. As a result, the endoscopes of the present invention can readily adapt and maintain a three-dimensional shape that effectively matches the natural configuration of the tract under examination.

The advantages of the endoscopes of the present invention are numerous and include reduced discomfort and thus reduced need for sedation medication.

For example, unlike prior endoscopes, the endoscopes of the present invention do not drag the balance of the endoscope along behind the distal end of the scope. Instead, the endoscopes of the present invention follow the shape of the lumen, minimizing stresses on the lumen walls.

Moreover, depending on manufacturing economics, the endoscopes of the present invention may be appropriate for single use, reducing the potential for re-use contamination.

DETAILED DESCRIPTION OF THE INVENTION

According to a preferred embodiment of the invention, an endoscope is constructed as an elongated body that contains numerous actuators, which are controlled by a computer. The endoscope has a sensing system at a distal end of the elongated body to sense the body lumen. The endoscope is steered utilizing the information from the sensing system to remain at or near the center of the lumen under examination. As the endoscope is advanced, the actuators are controlled such that the overall shape of the elongated body of the endoscope in 3-dimensional space reflects the natural (i.e., unstressed) shape of the lumen into which the endoscope is inserted, minimizing stress on the lumen. The endoscope follows the natural trajectory of the organ being examined. It is as if a wave, corresponding to the natural shape of the organ, travels along the endoscope as it is advanced, so that contact with, and stress upon, the lumenal walls, is minimized.

The actuators used in connection with the endoscopes of the present invention are electrically controlled actuators (as used herein, "electrically controlled actuators" include those actuators that are activated by photons) such as piezoelectric activators, shape memory activators and/or electroactive polymer actuators.

Actuators based on electroactive polymers, also referred to as "conducting polymers," are preferred. Electroactive polymers are a class of polymers which structurally feature a conjugated backbone and are electronically conductive. Some common electroactive polymers are polyaniline, polypyrrole and polyacetylene. Polypyrrole is pictured below:

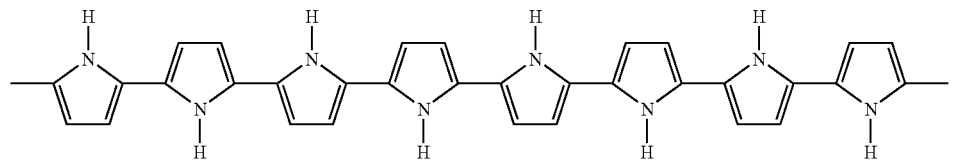

These materials are semi-conductors in their pure form. However, upon oxidation or reduction of the polymer, conductivity is increased. The oxidation or reduction leads to a charge imbalance which, in turn, results in a flow of ions into the material in order to balance charge. These ions, or dopants, enter the polymer from a surrounding, ionically conductive electrolyte medium. The electrolyte may be a gel, a solid, or a liquid. If ions are already present in the polymer when it is oxidized or reduced, they may exit the polymer.

In addition, it is well known that dimensional changes may be effectuated in certain conducting polymers by the mass transfer of ions into or out of the polymer. In some conducting polymers, the expansion is due to ion insertion between chains, whereas in others interchain repulsion is the dominant effect. Thus, the mass transfer of ions both into and out of the material leads to a contraction or expansion of the polymer.

Figure 1:
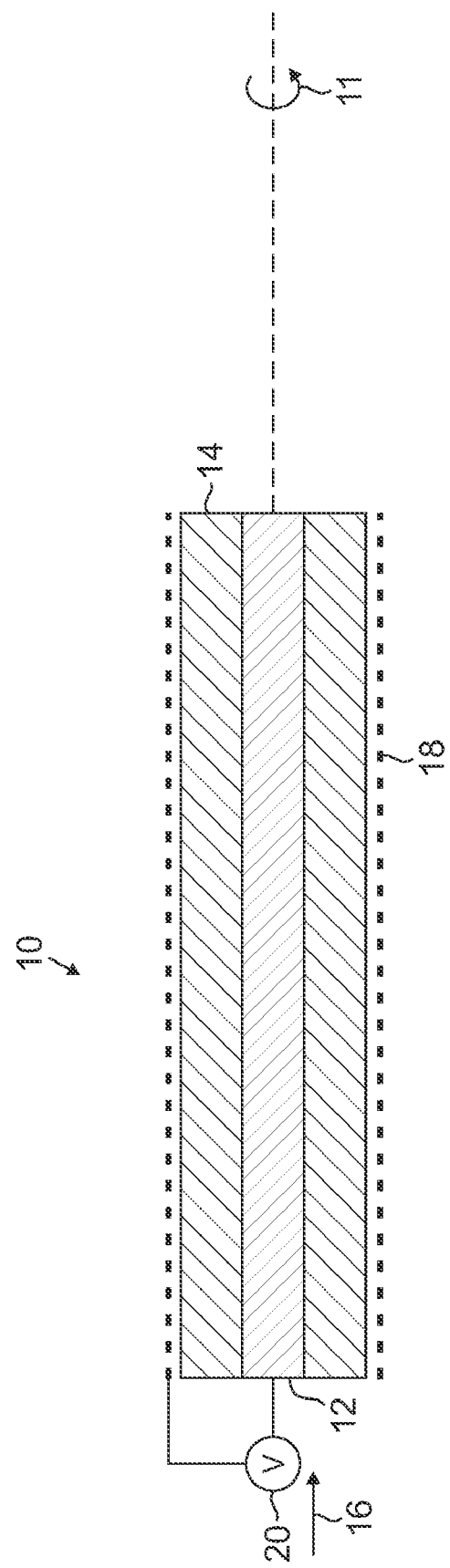
FIG. 1 is a schematic diagram of an actuator useful in the present invention.

Referring now to FIG. 1, an actuator 10 is shown schematically in cross-section. Active member 12 of actuator 10 has a surface coupled with electrolyte 14 and has an axis 11. Active member 12 includes a conducting polymer that contracts or expands in response to the flow of ions out of, or into, the active member 12. Ions are provided by electrolyte 14 which adjoins member 12 over at least a portion, and up to the entirety, of the surface of active member 12 in order to allow for the flow of ions between the two media. Many geometries are available for the relative disposition of member 12 and electrolyte 14. In accordance with preferred embodiments of the invention, member 12 may be a film, a fiber or a group of fibers, or a combination of multiple films and fibers disposed so as to act in consort for applying a tensile force in a longitudinal direction substantially along axis 11. The fibers may be bundled or distributed within the electrolyte 14.

Active member 12 includes an electroactive polymer. Many electroactive polymers having desirable tensile properties are known to persons skilled in the art. In accordance with preferred embodiments of the invention, active member 12 is a polypyrrole film. Such a polypyrrole film may be synthesized by electrodeposition according to the method described by M. Yamaura et al., "Enhancement of Electrical Conductivity of Polypyrrole Film by Stretching: Counter-ion Effect," Synthetic Metals, vol. 36, pp. 209-224 (1988), which is incorporated herein by reference. In addition to polypyrrole, any conducting polymer that exhibits contractile properties may be used within the scope of the invention. Polyaniline is an example of such a usable conducting polymer. Electrolyte 14 may be a liquid, a gel, or a solid. Preferably, the electrolyte 14 is a gel, for example, an agar or polymethylmethacrylate (PMMA) gel containing a salt dopant. Counter electrode 18 is in electrical contact with electrolyte 14 in order to provide a return path for charge to source 20 of potential difference between member 12 and electrolyte 14. Counter electrode 18 may be any electrical conductor, for example, another conducting polymer, a conducting polymer gel, or a metal such as gold. In order to activate actuator 10, a current is passed between active member 12 and counter electrode 18, inducing contraction or expansion of member 12. Additionally, the actuator may have a flexible skin for separating the electrolyte from an ambient environment.

Additional information regarding the construction of actuators, their design considerations, and the materials and components that may be employed therein, can be found, for example, in U.S. Pat. No. 6,249,076, assigned to Massachusetts Institute of Technology, and in Proceedings of the SPIE, Vol. 4329 (2001) entitled "Smart Structures and Materials 2001: Electroactive Polymer and Actuator Devices (see, in particular, Madden et al, "Polypyrrole actuators: modeling and performance," at pp. 72-83), both of which are hereby incorporated by reference in their entirety.

In general, as part of a failsafe mechanism for the devices of the present invention, it is beneficial that the actuators that are selected be of a type that relaxes in the event that power is interrupted.

The actuators can be disposed within the endoscopes of the present invention in a number of ways. For example, the actuators can be separately manufactured and subsequently attached to structural elements of the endoscopes. Alternatively, multiple actuators or actuator arrays can be disposed upon a sheet of material, for example, a polymeric sheet, which is associated with the endoscope.

Figure 2:
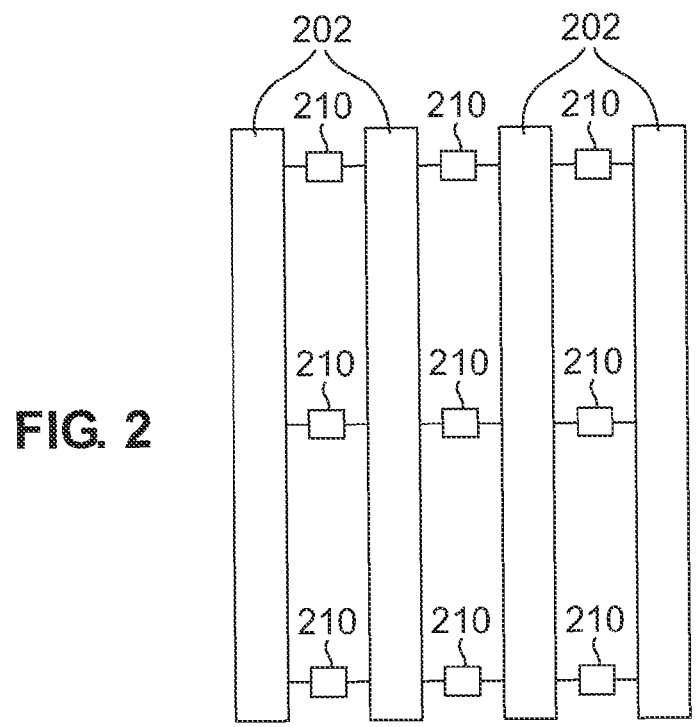
FIGS. 2-3 are schematic diagrams depicting some possible choices for the deployment of actuators with respect to the structural elements in the endoscopes of the present invention.

FIG. 2 illustrates one possible configuration of actuators and structural elements in accordance with the present invention, it being understood that the number of actuators and structural elements, as well as the spatial disposition of these elements with respect to one another, can vary widely from one embodiment to another. In the particular embodiment depicted, a series of four annular structural elements 202 are illustrated, with three actuators 210 disposed between each pair of structural elements 202.

Although not illustrated, the structure of FIG. 2 may be provided with a plurality of sensors, such as strain gauges, to provide electronic feedback concerning the orientation of the assembly. Preferably, each actuator provides position feedback through the intrinsic position-dependent electrical properties of the polymer: otherwise each actuator may be provided with a corresponding strain gauge. However, numerous variations are possible. Strain gauges suitable for use in the present invention include those in which the resistance of the device varies as a function of the amount of strain in the device, thus allowing the amount of strain to be readily quantified and monitored. Such strain gauges are commercially from a number of different sources, including National Instruments Co., Austin, Tex., and include piezoresistive strain gauges (for which resistance varies nonlinearly with strain) and bonded metallic strain gauges (for which resistance typically varies linearly with strain). The later strain gauges consist of very fine wire or metallic foil that is arranged in a grid pattern. The grid is bonded to a thin backing or carrier, which may be directly attached to the substrate being monitored for strain. Consequently, the strain experienced by the substrate is transferred directly to the strain gauge, which responds with a change in electrical resistance. Commercially available strain gauges typically have nominal resistance values within the range of 30 to 3000Ω, with 120Ω, 350Ω, and 1000Ω, devices being especially common.

The assembly is preferably further provided with a restoring force that biases the entire assembly toward a substantially linear configuration (although one skilled in the art will appreciate that the assembly may also be biased toward a non-linear configuration). In such an embodiment, the actuators may be used to deviate from this substantially linear configuration. A number of mechanisms can be provided to impart a suitable bias to the assembly. For example, the assembly can be inserted within an elastic sleeve (not shown), which tends to restore the system into a substantially linear configuration whenever any distorting forces applied by the actuators are not present. Alternatively, a series of springs (not shown) or other suitably elastic members can be disposed between the structural elements to restore the assembly to a substantially linear configuration. As another alternative, the structural elements within the assembly can be sufficiently elastic to restore the assembly to a substantially linear configuration. Once a biasing force is provided, the assembly can be bent into a number of configurations by simply contracting one or more of the actuators disposed between the various structural elements.

Figure 3:
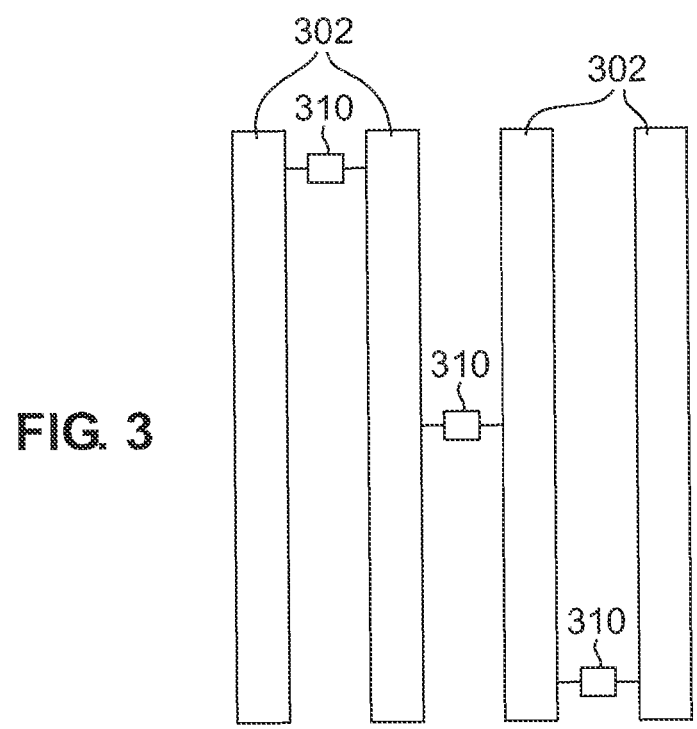

While the assembly depicted in FIG. 2 has the actuators disposed along three parallel axes, numerous variations based upon the above noted considerations are possible. For example, the actuators 310 between structural elements 302 can be deployed in a staggered arrangement as illustrated in FIG. 3.

Moreover, rather than providing the assembly with a biasing force that restores the entire assembly to a biased (e.g., substantially linear) configuration, a series of pivot points can be provided between the structural elements, if desired. In this way, the assembly can be bent into the desired configuration by placing at least two actuators in tension with one another. Hence, the actuators in a system of this type operate on a principle similar to the operation of skeletal muscles in living organisms such as snakes.

Figure 4:
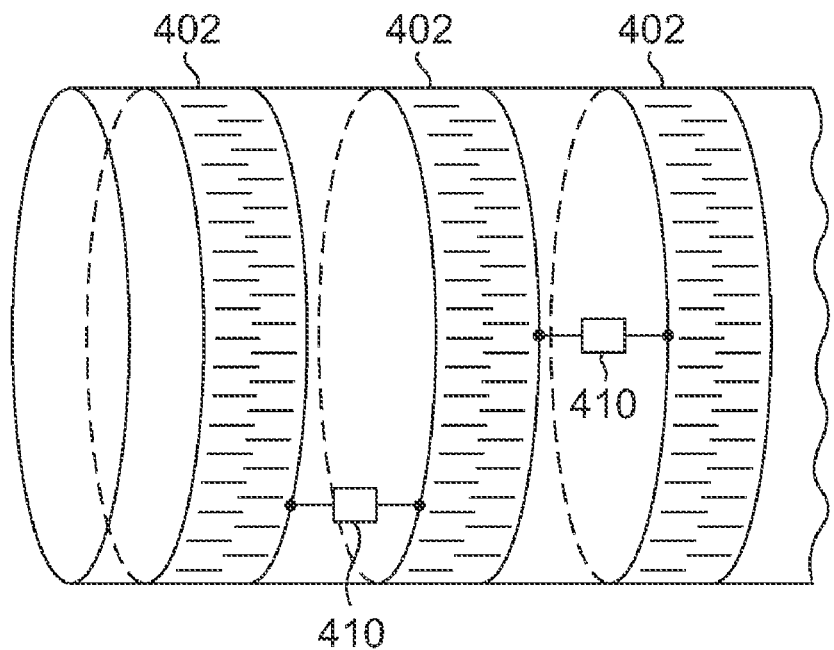
FIGS. 4-5 are perspective views of structural elements and actuators useful in the endoscopes of the present invention.

Moreover, a number of configurations and variations are possible with respect to the structural elements. For example, while the structural elements are depicted in FIGS. 2-4 as a series of closed loops, the structural elements can also include open loops, akin to the vertebrae structure of a snake. Moreover, the loops can be replaced by tubes of various lengths if desired. For example, a series of short tubes constructed in a fashion similar to known vascular, biliary or esophageal stents can be used. Such a structure is illustrated in FIG. 4, in which a plurality of actuators 410 are positioned between a series of short stent-like elements 402.

The structural elements may also be combined into a unitary structure.

Thus, for example, the discrete loops in some of the embodiments described above may be replaced by a single helical structural element, with the actuators deployed between adjacent turns of the helix. It is to be noted, however, that the adjacent turns of the helix act very much like the series of discrete loops depicted, for example, in FIG. 3.

Figure 5:
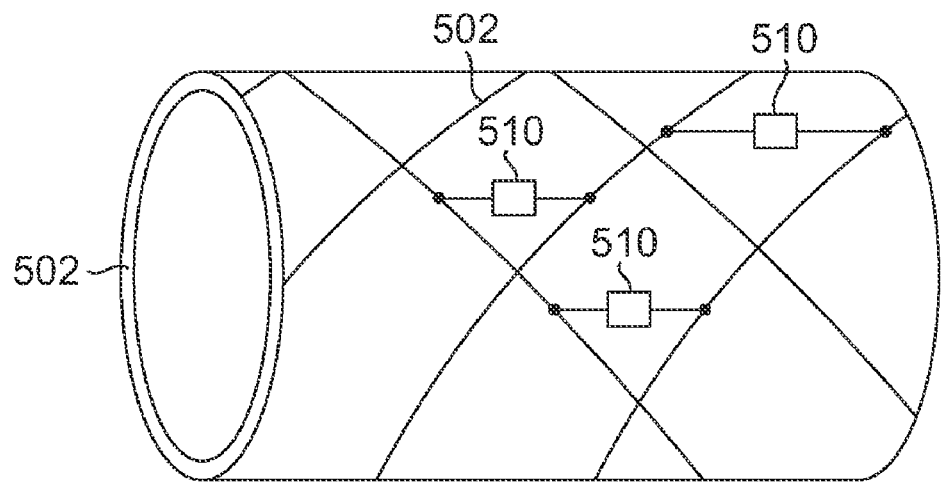

In other instances, a single elongated tube can be used as a structural element. As above, the designs for such structures can be in the form of stent-like elements. For example, referring to FIG. 5, actuators 510 can be disposed between adjacent members of a mesh structure 502. If a flexible or elastic material is used in the construction, the mesh structure 502 can be configured so that it will possess an inherent bias or memory that acts to restore the assembly to its original (e.g., substantially linear) configuration. The actuators 502 can then be used to deflect the structure from this configuration as needed to reflect the natural shape of the lumen into which the endoscope is inserted. Of course, a source of bias such as an elastic sleeve (shown here as being inserted within the mesh structure 502) can also be provided if desired.

Figure 6A:
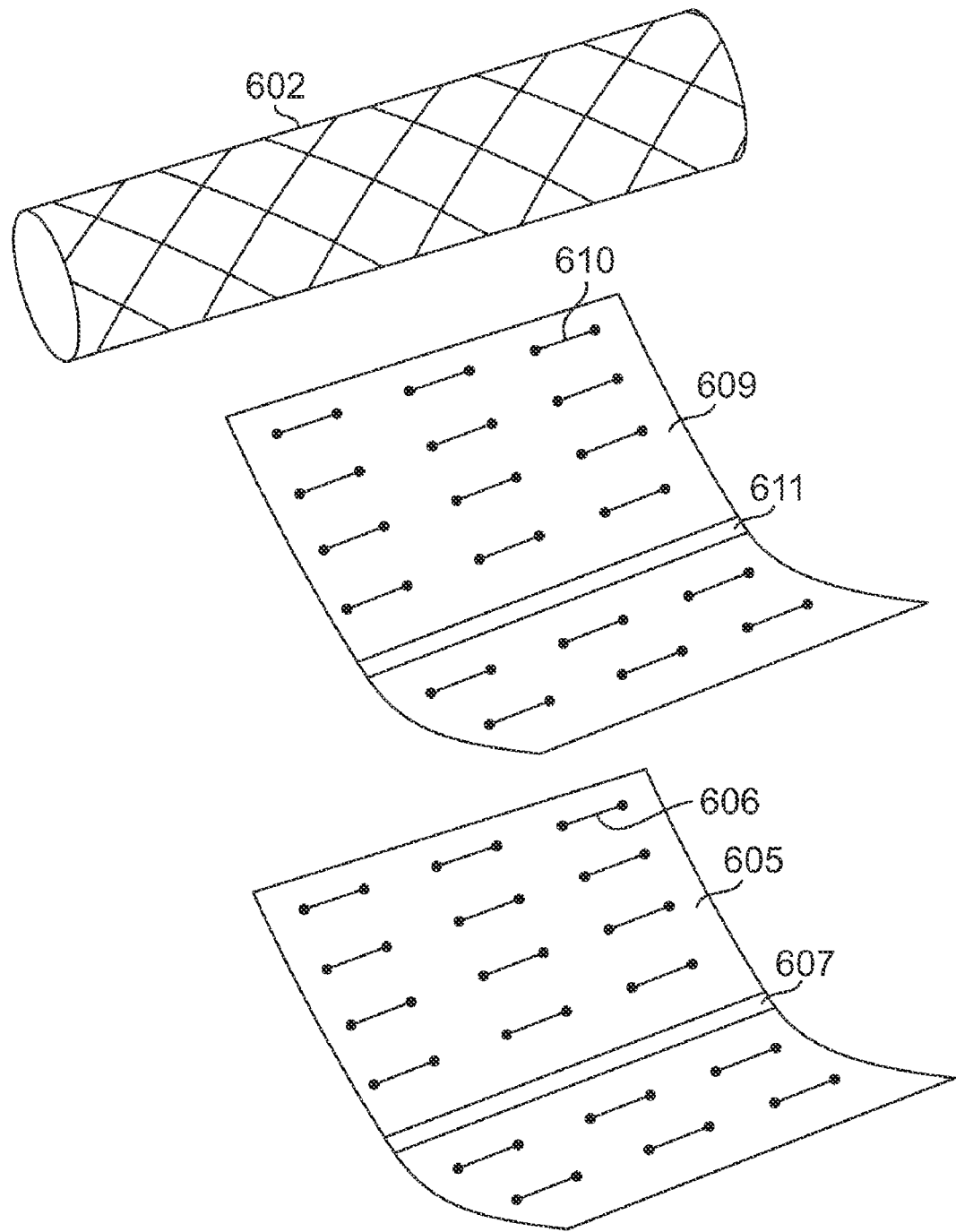
FIGS. 6A-B are perspective views of a structural element and associated components which are useful in the endoscopes of the present invention.

In the embodiments described above, the actuators are directly coupled to the structural elements. However, this need not be the case as illustrated, for example, in FIGS. 6A and 6B. FIG. 6A illustrates a structural element 602 which includes a wire mesh, and two flexible sheets 605 and 609. A series of actuators 610 (a single actuator is numbered) is printed on one sheet 609, along with a control bus 611 for transmitting control signals to the actuators 610 from a controlling device (individual interconnections with actuators 610 are not illustrated). A plurality of strain gauges or feedback polymer elements 606 (a single strain gauge is numbered) is printed on the other sheet 605, along with a readout bus 607 for transmitting information from the strain gauges 606 (individual interconnections with strain gauges 606 are not illustrated) to a controlling device.

Preferably, the two sheets employed in the structural element comprise elastomeric materials such as, for example, styrene-butadiene copolymers, polychloroprene, nitrile rubber, butyl rubber, polysulfide rubber, cis-1,4-polyisoprene, ethylene propylene terpolymers, silicone rubber, or polyurethane rubber. Alternatively the sheets may be constructed from stiffer polymers like those used in electronic printed circuits or cables, such as polyimide (e.g., Kapton®), and relieved by selective cutting, e.g. with a laser, to provide the appropriate flexibility. The sheets are registered with one another and the layers are bonded together to form a unitary mass using suitable means as are known to the art. Such means may include, for example, lamination, spot welding, interlayer electrical connections similar to the plated-through holes of multiplayer printed circuits, the use of an adhesive layer or a tie layer, and so forth.

Figure 6B:
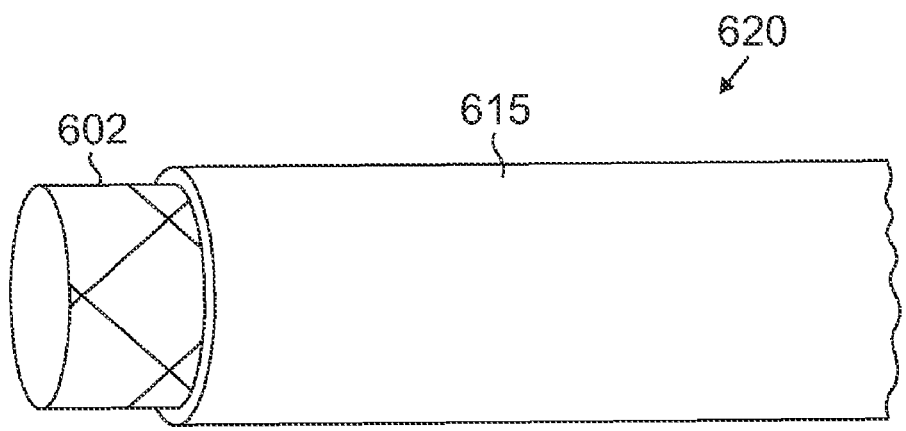

The bonded structure 615 is then wrapped around the structural element 602, and the edges are joined to provide a cylindrical assembly 620 as illustrated in FIG. 6B. A protective sheath may be disposed over the assembly, if desired. In this design, the structural element 602, the bonded structure 615 or both will act to bias the overall assembly 620 in a preferred configuration, which will typically be a linear configuration. The actuators 610 are used to deflect this structure to the desired degree, while the strain gauges 606 provide feedback regarding the extent of the deflection.

Figure 7:
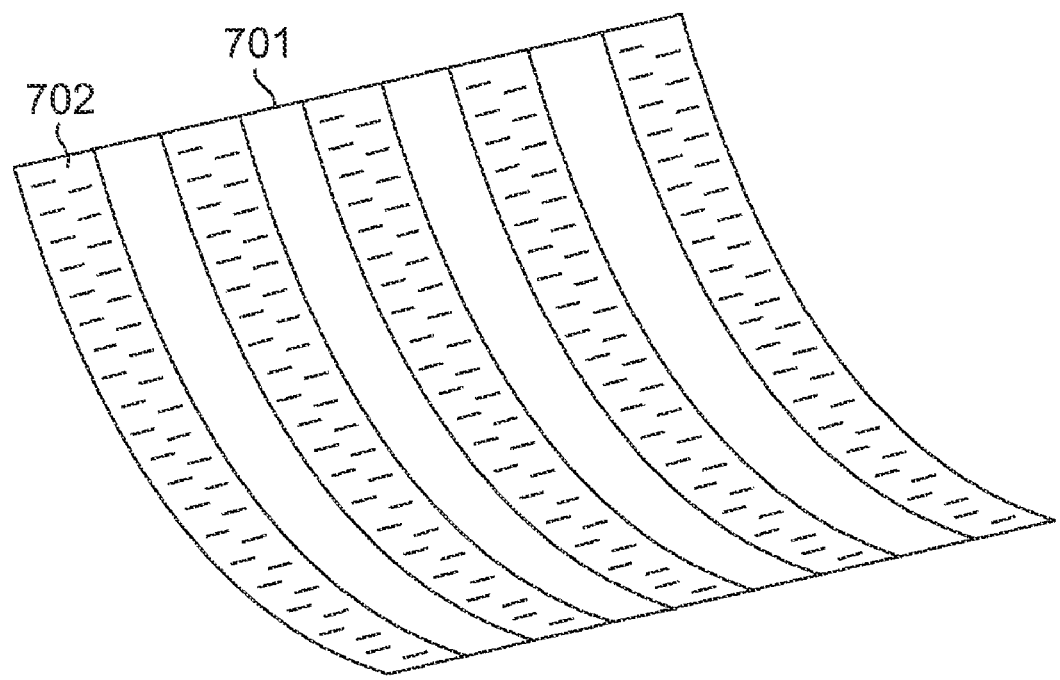
FIG. 7 is a perspective view of a sheet with structural elements incorporated therein.

If desired, the structural elements, as well as the strain gauges 606 and actuators 610, can also be provided in the form of a printed sheet. For example, FIG. 7 illustrates sheet 701 having printed thereon a series of relatively stiff structural elements 702 which, when rolled up, will form structural elements similar to those illustrated in FIG. 4.

Figure 8A:
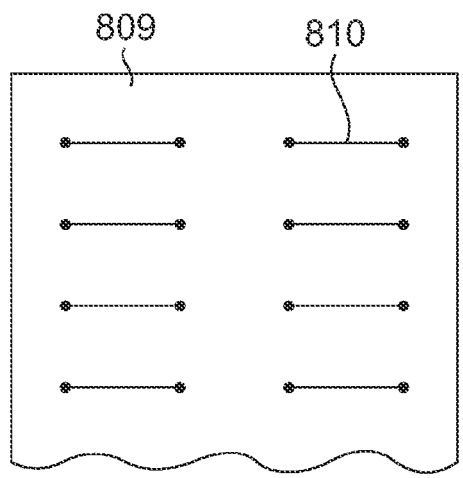
FIGS. 8A-C are top views illustrating some possible orientations of actuators on a substrate.
Figure 8B:
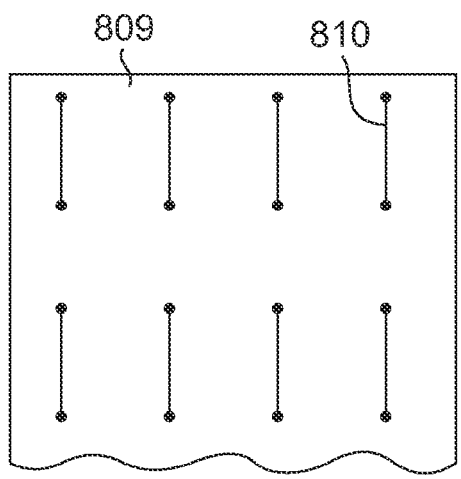
Figure 8C:
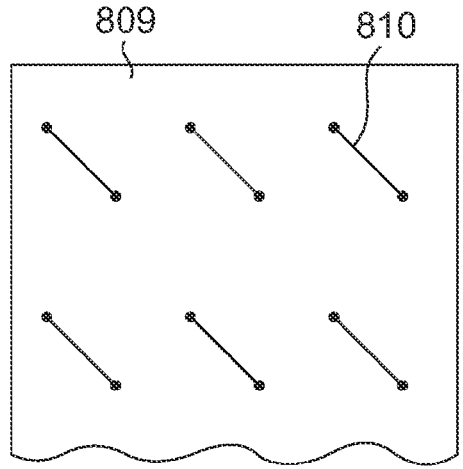

In general, the activators are oriented in the direction needed for control, somewhat like the muscles of a snake. For example, FIGS. 8A, 8B and 8C illustrate three sheets 809, each having a series of actuators 810 (one actuator is numbered in each figure), which are oriented in various directions. By laminating these sheets together, a laminated structure (not shown) can be created which can bend, contract circumferentially, and so forth.

Each actuator and strain gauge within the endoscopes of the present invention is preferably in communication with, and is individually controllable by, a computer or other suitable controlling device. This allows the controlling device to monitor these elements and to perform operations on them for the purpose of effecting changes to the configuration of the overall device.

The actuators and strain gauges may be in direct communication with the controlling device by means of dedicated circuits linking each of these elements to the controlling device. However, it is more preferred to deploy these elements in an array in which each element is in communication with the controlling device by means of a common communications cable. The signals from each element may be digital or analog. If need be, digital-to-analog or analog-to-digital converters may be provided to convert the signals from one format to the other.

The signals from each element may be conveniently managed and transmitted over the common cable by multiplexing. Multiplexing schemes that may be used for this purpose include frequency-division multiplexing, wave-division multiplexing, or time-division multiplexing. Suitable multiplexers and demultiplexers can be employed at each end of the cable and along its length at the position of each actuator or gage.

In terms of electronic data storage, each actuator and strain gauge may be given a separate address in electronic memory where information concerning the state of the element is stored. This information may be accessed to determine the state of the device, or for the purpose of performing operations on the device or its elements. The memory in which the information is stored may be of a volatile or non-volatile type, and may be in the device itself and/or may be in or associated with the controlling device. Thus, for example, if there are 16 actuators and 16 strain gauges in each module and 256 modules in the entire endoscope, then there will be 256×32 or $2^{13}$ addresses. These components can thus be addressed using, for example, a 16-bit cable and a decoder.

Numerous cable configurations are possible. For example, the cables can be directly connected to the actuators. Alternatively, the cables can be printed onto a sheet. Each flat sheet upon which the actuators and strain gauges are printed may be similar to a flexible printed circuit board in that the necessary elements are printed upon a flexible substrate. Each layer can be provided with its own track wires and control cables (e.g., the readout and control buses discussed above). Alternatively, the actuators and strain gauges can be connected to a separate interconnect layer, for example, by plated through-holes or vias (these also function as "rivets" to hold the composite together). These through-holes can tie into a series of conductive track wires disposed on the interconnect layer, which track wires connect to a "spinal cord", such as a cable bundle, flat cable or ribbon cable that runs the length of the device.

The endoscopes of the present invention are typically provided with a slippery, lubricious coating to assist in its advancement into the lumen of interest. Lubricious coatings are known in the art and include, without limitation, hydrogel coatings, silicones, and fluoropolymers such as polytetrafluoroethylene.

The sensing system used in the endoscope preferably comprises a light source and an imaging system at or near its distal end. For example, the light source can be a white-light-emitting laser diode or a fiber optic light source such as a bundle of optical fibers with a diffuser at the distal end. The imaging system can be, for example, an optical fiber or a camera, such as CCD camera chip or CMOS camera chip. Of course, other light-based and non-light-based systems are possible, operating in the visible or other regions of the spectrum, using reflected radiation or fluorescence, sensing endogenous or exogenous (e.g., contrast-agent dye induced) responses, and including other imaging modalities like ultrasound or optical coherence tomography.

The endoscopes of the present invention are also provided with features that are common to traditional endoscopes. For example, the endoscopes can be provided with channels for lavage (e.g., a tube for saline delivery) and insufflation (e.g., a tube for expending carbon dioxide). Moreover, a working channel is typically provided, which extends through the elongated body and allows surgical instruments used in conventional endoscopes to be advanced to distal end. Such instruments include biopsy probes (e.g., snares or baskets), biopsy forceps, and electrosurgery probes (e.g., fulguration probes for RF ablation).

Any number of techniques can be used to advance the endoscope into the body lumen. For example, the endoscope can be manually inserted as is the practice with traditional endoscopes. The manual insertion can either be direct (e.g., by means of a control handle) or by operation of a manual drive mechanism (e.g., by operation of a crank). The endoscope may also be advanced by a drive mechanism (e.g., an electric servo payout motor) using a drive algorithm. The preferred techniques of the present invention, however, do not involve any form of internal anchoring, which could cause discomfort in the individual to be examined.

The distance of endoscope advancement is monitored in accordance with the present invention. Numerous methods can be used for this purpose. For instance, various depth gauges or linear displacement transducers can be used. As one example, a depth gauge can be supplied, which contains a rotating gear wheel whose revolutions are monitored. As another example, a linear displacement transducer containing a depth code which can be read optically (using, for example, bar-codes and an optical source and detector) or magnetically (using, for example, a magnetic code and a Hall effect sensor) can be used to determine the extent of endoscope advancement. These and numerous other known methods are available for determining advancement distance.

Figure 9:
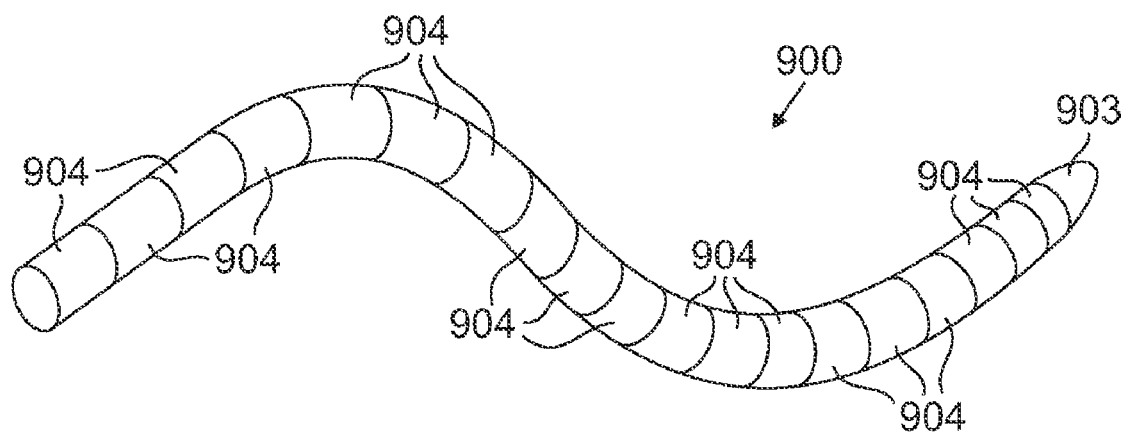
FIG. 9 is a perspective view of the body portion of an endoscope in accordance with the present invention.
Figure 10:
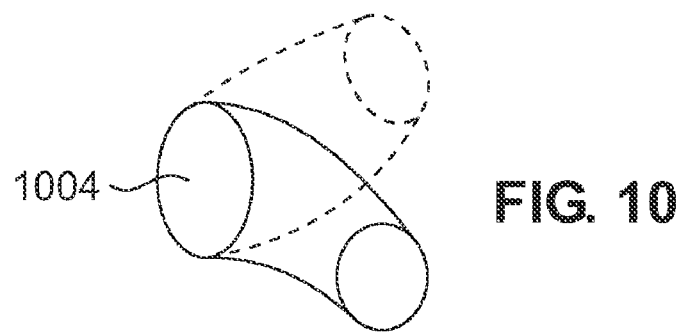
FIG. 10 is a perspective view of an endoscope module in accordance with the present invention.

The endoscopes of the present invention are preferably divided into a series of "deflection modules", each of which includes a plurality of actuators that allow the module to take on a variety of shapes in 3-dimensional space in response to input by the control device. The greater the number of modules, the finer the control of the 3-dimenisonal orientation of the endoscope. A simplified schematic diagram of an endoscope 900 with eighteen modules 904 and a working tip 903 is found in FIG. 9. The overall shape of the endoscope is established by manipulating the deflection among each of the modules. As illustrated in FIG. 10, the actuators can be activated to deflect a given module 1004 from a first position (designated by solid lines) to a second position (designated by dashed lines). As one specific example, a module can consist of a group of actuators between two or more structural elements as discussed above, allowing the module to be bent in an up, down, left or right fashion. Of course, myriad other options are available. Additional degrees of freedom in deflection are also possible, e.g., changes in diameter for expansion or contraction, as might be used to deliver stents; or changes in length, as might be used for propulsion or access.

Figure 11:
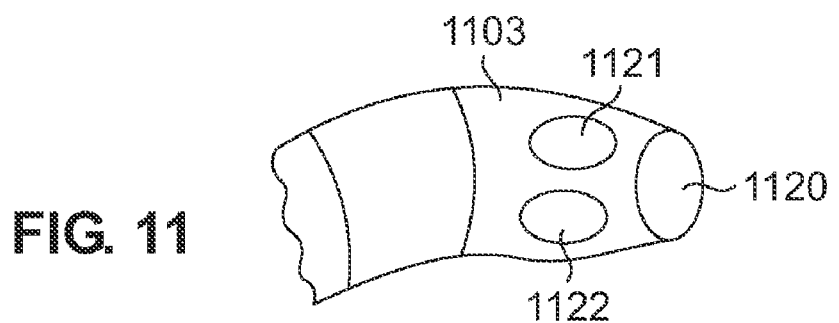
FIG. 11 is a perspective view of the distal end of an endoscope in accordance with the present invention.

FIG. 11 provides a more detailed schematic view of one working tip 1103, which includes a white-light-emitting laser diode 1121, a CCD camera 1122 and a working channel 1120.

The curvature of each module is typically modified by the voltage that is applied to each actuator. As noted above, the endoscope is preferably provided with a plurality of strain gauges that provide a sensing function for electronic feedback. This electronic feedback will provide a number of advantages, including greater stability, error correction, and immunity from drift. More preferably, a strain gauge is provided for each actuator in the endoscope. To the extent that the behavior of the actuator in response to an electronic input is highly predictable, however, electronic feedback will not be necessary.

The endoscope is provided with a steering system, which is used to control electronic actuators in a working tip (also referred to herein as the "lead module") of the endoscope. A number of options are available for carrying out this task. For example, the endoscope can be provided with a manual steering system that is operated under image guidance. For example, electrical control from the computer can be based on manual steering input using a joystick or the like. The joystick or the like is manipulated by an operator based on an image provided from the distal end of the endoscope. The operator will typically endeavor to maintain the lead module at the center of the body lumen.

As another example, based on input from a sensing system like that discussed above, electrical control can be provided by means of a edge-tracking or center-seeking algorithm to keep the distal end of the endoscope at the center of the body lumen.

In many preferred embodiments, the endoscope will be steered in a semiautomatic fashion, for example, using a computer algorithm like that discussed above to suggest a direction of travel, with a trained operator acting to either accept or reject the computer-generated suggestion. In this instance, it may be desirable to tailor the algorithm to reflect operator preferences based upon operator profiles, which can include examination histories and databases, preferably web-enabled.

Once a position of interest is reached, the working tip applies specific diagnostic or therapeutic functions, just as in conventional endoscopy.

As the endoscope is advanced into the body lumen, a 3-dimensional representation the desired shape of the endoscope is stored into memory, with further data being added with increasing depth of insertion.

According to one preferred embodiment, the orientation of the lead module as a function of advancement distance is stored to the computer, acting as a map for subsequent deflection modules. The distance data can be provided, for example, from a depth gauge or linear displacement transducer as described above. The data relating to the orientation of the lead module can be provided, for example, using input from a steering step (e.g., input from a joystick or input from a center-seeking computer algorithm) or from position sensors or strain gauges. Using this map, electrical control signals for the actuators are calculated as a function of insertion depth. As a result, as subsequent modules arrive at the position that was previously occupied by the lead module, the actuators within these modules are operated such that they take the orientation of the lead module when it was present at that particular depth of insertion.

Figure 12A:
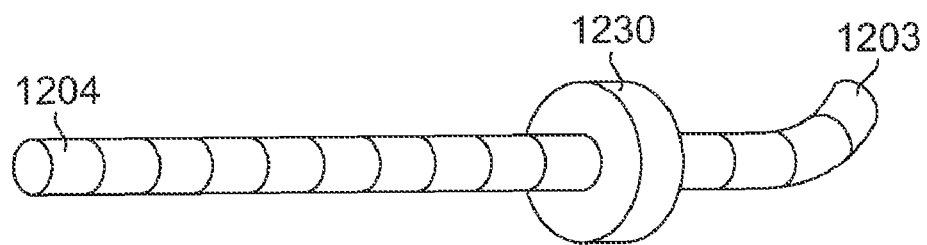
FIGS. 12A-C are perspective views illustrating the ability of the endoscopes of the present invention to retain their orientation at a given depth of insertion.
Figure 12B:
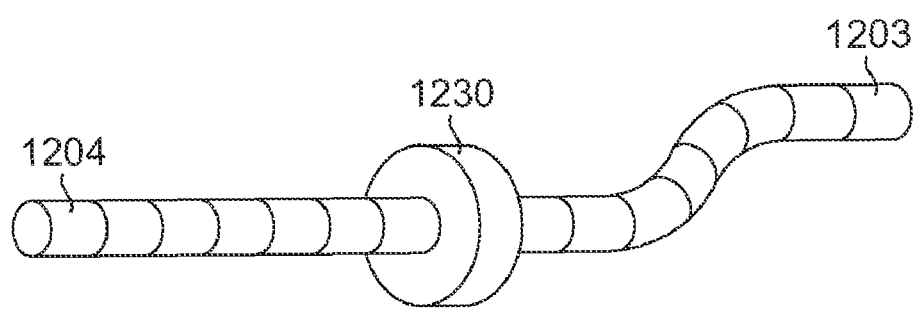
Figure 12C:
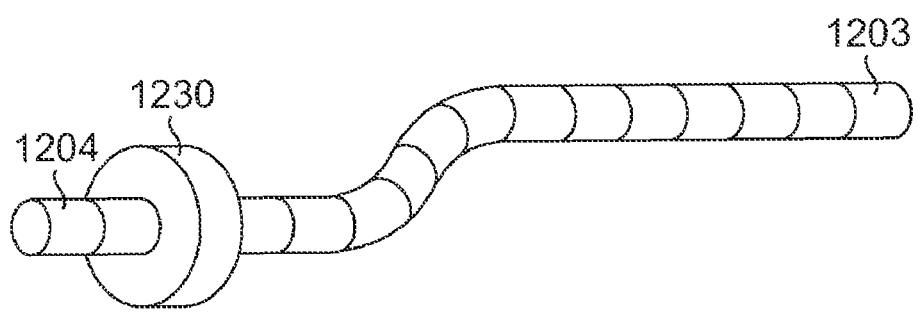

The result of the above is that the endoscope retains its path in 3-dimensional space, reflecting the shape of the tract (trajectory) that it travels through. This is illustrated in FIG. 12, which contains a simplified schematic diagram of an endoscope, consisting of a number of deflection modules 1204 (one numbered) and a working tip 1203, as well as a linear displacement transducer 1230, which is provided, for example, at the point of insertion. These figures illustrate the orientation of the endoscope: shortly after insertion (FIG. 12A), at an intermediate point of insertion (FIG. 12B) and at a point of full insertion (FIG. 12C). As seen from these figures, as it advances, the endoscope retains its orientation at a given depth of insertion.

Figure 13:
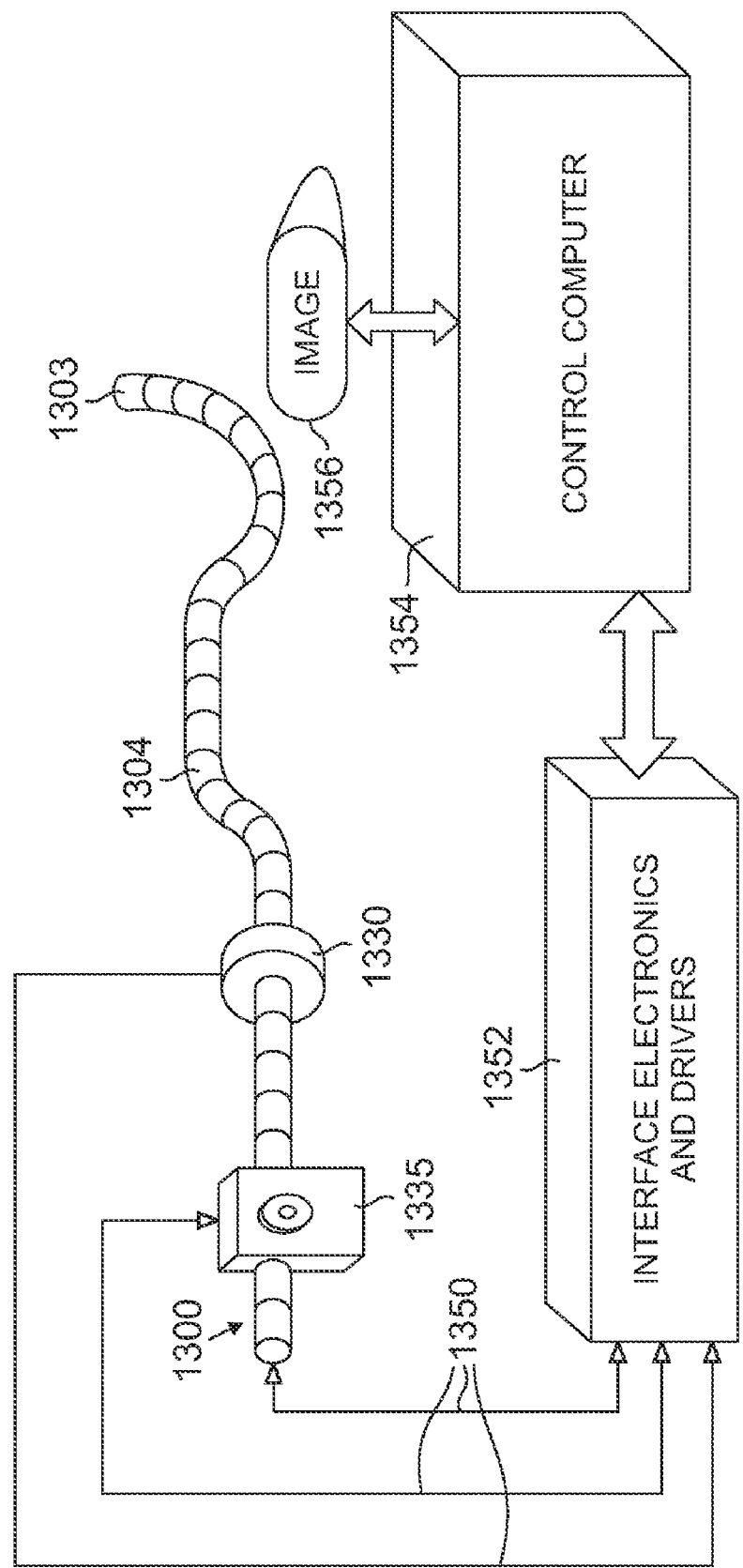
FIG. 13 is a schematic drawing of an endoscopic assembly in accordance with the present invention.

FIG. 13 is a simplified schematic diagram of an endoscopic system in accordance with an embodiment of the invention. As discussed above, the endoscopic system includes an endoscope containing a working tip 1303 and a number of deflection modules 1304 (one numbered). The endoscope is advanced via electric servo payout motor 1335, with data concerning the degree of advancement being provided by linear displacement transducer 1330. Electronic cables 1350 are provided between an electronic interface (including drivers) 1352 and the endoscope 1300, the payout motor 1335 and the linear displacement transducer 1330. Signals are output and sent to the interface 1352 through these cables from the linear displacement transducer 1330 as well as, for example, the strain gauges and CCD camera found in the working tip 1303. Signals are sent from drivers in the electronic interface 1352 through these cables 1350 to the electric servo payout motor 1335 as well as, for example, actuators and illumination means within the endoscope 1300. A control computer 1354, along with the electronic interface 1352, provide servo control of the 3-dimensional shape of the endoscope 1300 as it is advanced. A monitor 1356 provides the operator with a view from the distal end of the endoscope.

Further aspects include the following enumerated aspects, among others:

Aspect 1. An endoscope, comprising: (a) an elongated body adapted for insertion into an lumen; and a plurality of electrically controlled actuators associated with said body, said actuators being controllable to impart a desired orientation to said body that reflects the natural orientation of the lumen into which the endoscope is inserted.

Aspect 2. The endoscope of aspect 1, further comprising a sensing system at a distal end of the elongated body for sensing the natural orientation of the lumen into which the endoscope is inserted.

Aspect 3. The endoscope of aspect 1, wherein said endoscope is adapted to maintain an orientation that is complimentary to the natural orientation of the lumen as the endoscope is advanced into the lumen.

Aspect 4. The endoscope of aspect 1, wherein said actuators are controllable to provide a desired curvature to said body in 3-dimensional space at each of a plurality of loci along the length of said body.

Aspect 5. The endoscope of aspect 2, wherein said sensing system is an optical system.

Aspect 6. The robotic endoscope of aspect 5, wherein said optical system comprises a light source and a camera.

Aspect 7. The endoscope of aspect 1, further comprising lavage and insufflation tubes.

Aspect 8. The endoscope of aspect 1, wherein said body is adapted to be manually advanced.

Aspect 9. The endoscope of aspect 1, wherein said endoscope further comprises a drive mechanism for advancing the body through the lumen in accordance with a drive algorithm.

Aspect 10. The endoscope of aspect 1, further comprising a depth gauge.

Aspect 11. The endoscope of aspect 1, further comprising a linear displacement transducer.

Aspect 12. The endoscope of aspect 1, further comprising a plurality of strain gauges.

Aspect 13. The endoscope of aspect 1, wherein said electrically controlled actuators are electroactive polymer actuators.

Aspect 14. The endoscope of aspect 13, wherein said electroactive polymer actuators comprise an electroactive polymer selected from the group consisting of polyaniline, polypyrrole, and polyacetylene.

Aspect 15. The endoscope of aspect 14, wherein said electroactive polymer is polypyrrole.

Aspect 16. The endoscope of aspect 1, further comprising a lubricious layer disposed on the outer surface of said body.

Aspect 17. The endoscope of aspect 1, wherein said elongated body is provided with a restoring force to bring it into alignment with its longitudinal axis, and wherein said elongated body deviates from such alignment when said actuators are in a contracted state.

Aspect 18. The endoscope of aspect 17, further comprising a plurality of structural elements, wherein said restoring force is provided by a plurality of springs disposed between structural elements.

Aspect 19. The endoscope of aspect 17, further comprising a plurality of structural elements, and wherein said restoring force is provided by an elastic cover disposed over said structural elements.

Aspect 20. The endoscope of aspect 17, further comprising a plurality of elastic structural elements, wherein said restoring force is provided by the structural elements.

Aspect 21. The endoscope of aspect 13, wherein said electroactive polymer actuators are attached to pairs of structural elements.

Aspect 22. The endoscope of aspect 1, further comprising a plurality of structural elements, wherein said structural elements are selected from the group consisting of (a) an open-mesh network comprising at least one metallic filament, (b) an interconnected network of articulable segments, (c) a helical structure comprising at least one metallic filament, and (d) a patterned tubular sheet.

Aspect 23. The endoscope of aspect 1, further comprising a plurality of structural elements, wherein said structural elements comprise a series of short tubes.

Aspect 24. The endoscope of aspect 13, wherein said electroactive polymer actuators are disposed on at least one sheet that is rolled into an actuator tube.

Aspect 25. The endoscope of aspect 24, further comprising a plurality of tubular structural elements, and wherein each of said actuator tubes is disposed outside or within at least one of said tubular structural elements.

Aspect 26. The endoscope of aspect 25, wherein each of said plurality of tubular structural elements is selected from the group consisting of (a) an open-mesh network comprising at least one knitted, woven or braided metallic filament, (b) an interconnected network of articulable segments, (c) a helical structure comprising at least one metallic filament, and (d) a patterned tubular sheet.

Aspect 27. The endoscope of aspect 1, further comprising a plurality of structural elements, and wherein said structural elements are disposed on at least one sheet that is rolled into the form of a tube.

Aspect 28. The endoscope of aspect 27, further comprising a plurality of strain gauges and actuators that are disposed on at least one sheet.

Aspect 29. The endoscope of aspect 1, wherein each of said actuators is connected to a controlling device by way of an individual cable.

Aspect 30. The endoscope of aspect 1, wherein each of said actuators is connected to a controlling device by way a multiplexed cable.

Aspect 31. The endoscope of aspect 1, wherein each of said actuators is connected to a controlling device by way of interconnection lines that are printed on one or more flexible sheets.

Aspect 32. The endoscope of aspect 1, wherein said endoscope is equipped with a manual steering system that is operated under image guidance.

Aspect 33. The endoscope of aspect 1, wherein said endoscope is equipped with an automated or semi-automated steering system comprising a lumen-center-seeking algorithm.

Aspect 34. The endoscope of aspect 1, wherein said body comprises a lead module and a plurality of subsequent modules, and wherein said endoscope is adapted to travel through lumen in such a way that, when each subsequent module reaches a position in the lumen previously occupied by said lead module, said actuators cause said each subsequent module to replicate the orientation of the lead module at said position.

Aspect 35. The endoscope of aspect 34, wherein data regarding said position is provided by a depth gauge of a linear displacement module.

Aspect 36. The endoscope of aspect 34, wherein data regarding said lead module orientation is provided by strain gauges disposed in said lead module.

Aspect 37. The endoscope of aspect 1, wherein the lumen is an intestinal lumen.

Aspect 38. An endoscopic procedure, comprising: (a) providing the endoscope of aspect 1; and (b) inserting the endoscope into a body lumen while controlling said actuators to impart said desired orientation to the elongated endoscope body.

Aspect 39. An endoscopic procedure, comprising: (a) providing the endoscope of aspect 2; and (b) inserting the endoscope into a body lumen while controlling said actuators to impart said desired orientation to the elongated endoscope body.

Aspect 40. An endoscopic procedure, comprising: (a) providing the endoscope of aspect 13; and (b) inserting the endoscope into a body lumen while controlling said actuators to impart said desired orientation to the elongated endoscope body.

Aspect 41. An endoscopic procedure, comprising: (a) providing the endoscope of aspect 22; and (b) inserting the endoscope into a body lumen while controlling said actuators to impart said desired orientation to the elongated endoscope body.

Aspect 42. An endoscopic procedure, comprising: (a) providing the endoscope of aspect 33; and (b) inserting the endoscope into said intestinal lumen while controlling said actuators to impart said desired orientation to the elongated endoscope body.

Although the present invention has been described with respect to several exemplary embodiments, there are many other variations of the above-described embodiments that will be apparent to those skilled in the art, even where elements have not explicitly been designated as exemplary. It is understood that these modifications are within the teaching of the present invention, which is to be limited only by the claims appended hereto.

What is claimed is:

1. An EAP actuator assembly comprising a first plurality of electroactive polymer actuators disposed upon a first flexible sheet and a second plurality of electroactive polymer actuators disposed upon a second flexible sheet, wherein said first and second flexible sheets are fixed together, wherein the first and second flexible sheets are in the form of a tube, and wherein the first plurality of said electroactive polymer actuators disposed upon said first flexible sheet is oriented in a different direction from the second plurality of said electroactive polymer actuators disposed upon said second flexible sheet.

2. The EAP actuator assembly of claim 1, wherein said electroactive polymer actuators comprise an electroactive polymer selected from the group consisting of polyaniline, polypyrrole, and polyacetylene.

3. The EAP actuator assembly of claim 1, wherein each of said electroactive polymer actuators is connected to a controlling device by way of interconnection lines that are printed on said first and second flexible sheets.

4. The EAP actuator assembly of claim 1, wherein the first and second flexible sheets are positioned around a tubular structural member.

5. The EAP actuator assembly of claim 4, wherein said tubular structural member further comprises a plurality of tubular structural elements.

6. The EAP actuator assembly of claim 5, wherein said structural elements comprise a series of short tubes.

7. The EAP actuator assembly of claim 5, wherein said structural elements are disposed on one or more flexible sheets that are in the form of a tube.

8. The EAP actuator assembly of claim 4, further comprising a plurality of sensors that are adapted to provide feedback regarding the orientation of the tubular structural member.

9. The EAP actuator assembly of claim 8, wherein said sensors are strain gauges.

10. The EAP actuator assembly of claim 8, wherein said sensors are disposed upon one or more flexible sheets that are in the form of a tube.

11. The EAP actuator assembly of claim 8, wherein said sensors are disposed on said first and second flexible sheets along with said electroactive polymer actuators.

12. The EAP actuator assembly of claim 4, wherein the electroactive polymer actuators on said first flexible sheet are aligned with the longitudinal axis of said tubular structural member, and wherein the electroactive polymer actuators on said second flexible sheet range from about 45 to about 90 degrees out of alignment with the longitudinal axis of said tubular structural member.

13. The EAP actuator assembly of claim 1, wherein said electroactive polymer actuators are disposed on inner surfaces of said tubes.

14. The EAP actuator assembly of claim 1, wherein each of said electroactive polymer actuators is connected to a controlling device by way of an individual cable.

15. The EAP actuator assembly of claim 1, wherein each of said electroactive polymer actuators is connected to a controlling device by way a multiplexed cable.

16. The EAP actuator assembly of claim 1, wherein said first and second flexible sheets are spot welded to one another.

17. The EAP actuator assembly of claim 1, wherein said first and second flexible sheets are laminated to one another.

18. The EAP actuator assembly of claim 1, wherein the electroactive polymer actuators on said first flexible sheet are aligned with the longitudinal axis of the tube, and wherein the electroactive polymer actuators on said second flexible sheet range from about 45 to about 90 degrees out of alignment with the longitudinal axis of the tube.

* * * * *